(12) United States Patent
Wei

(10) Patent No.: US 8,586,322 B2
(45) Date of Patent: Nov. 19, 2013

(54) SANDWICH ASSAY FOR IMMUNOSUPPRESSANT DRUGS

(75) Inventor: Tie Quan Wei, Wilmington, DE (US)

(73) Assignee: Siemens Healthcare Diagnostics, Inc, Tarrytown, NY (US)

( * ) Notice: Subject to any disclaimer, the term of this patent is extended or adjusted under 35 U.S.C. 154(b) by 92 days.

(21) Appl. No.: 13/413,925

(22) Filed: Mar. 7, 2012

(65) Prior Publication Data

US 2013/0236918 A1  Sep. 12, 2013

(51) Int. Cl.
*G01N 33/53* (2006.01)
*G01N 33/553* (2006.01)

(52) U.S. Cl.
USPC ............... 435/7.94; 436/518; 436/525

(58) Field of Classification Search
None
See application file for complete search history.

(56) References Cited

U.S. PATENT DOCUMENTS

| | | | |
|---|---|---|---|
| 4,628,037 A | 12/1986 | Chagnon et al. | |
| 6,136,545 A | 10/2000 | Hosel et al. | |
| 7,592,186 B2 | 9/2009 | Drengler et al. | |
| 7,749,773 B2 | 7/2010 | Day et al. | |
| 7,790,401 B2 | 9/2010 | Wei et al. | |
| 7,883,855 B2 | 2/2011 | Grenier et al. | |
| 7,910,378 B2 | 3/2011 | Wei et al. | |
| 8,030,458 B2 | 10/2011 | Kasper et al. | |
| 2009/0087865 A1 | 4/2009 | Kasper et al. | |
| 2010/0297670 A1 | 11/2010 | Wei et al. | |
| 2011/0318754 A1 | 12/2011 | Wei | |

OTHER PUBLICATIONS

International Search Report for PCT/US2013/024054 dated Apr. 19, 2013.

*Primary Examiner* — Shafiqul Haq
*Assistant Examiner* — Galina Yakovleva
(74) *Attorney, Agent, or Firm* — Theodore Leiterig

(57) ABSTRACT

Methods are disclosed for determining an immunosuppressant drug in a sample suspected of containing an immunosuppressant drug. The method includes providing in combination in a medium the sample, a first monoclonal antibody for the immunosuppressant drug, and a second monoclonal antibody for the immunosuppressant drug. The second monoclonal antibody binds to a portion of the immunosuppressant drug other than the portion to which the first monoclonal antibody binds to the immunosuppressant drug. The medium is incubated under conditions for binding of the first monoclonal antibody and the second monoclonal antibody to the immunosuppressant drug. The medium is examined for the presence of an immunocomplex comprising the immunosuppressant drug, the first monoclonal antibody and the second monoclonal antibody. The presence and/or amount of the immunocomplex indicates the presence and/or amount of the immunosuppressant drug in the sample.

12 Claims, 4 Drawing Sheets

SANDWICH ASSAY FOR IMMUNOSUPPRESSANT DRUGS

BACKGROUND

The invention relates to compounds, methods and kits for the determination of immunosuppressant drugs, in samples, such as patient samples, known or suspected to contain one or more of such immunosuppressant drugs.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are therapeutic drugs that are carefully administered to transplant recipients in order to help prevent allograft rejection of non-self tissue. Immunosuppressive drugs can be classified as follows: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins, the latter of which specifically bind, for example, tacrolimus or sirolimus.

Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also useful as immunosuppressants. Such derivatives include, for example, Everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because distribution and metabolism of an immunosuppressant drug can vary greatly between patients and because of a wide range and severity of adverse reactions, accurate monitoring of the drug level is essential.

There is, therefore, a continuing need to develop fast and accurate diagnostic methods to measure levels of immunosuppressant drugs or derivatives thereof in patients. The methods should be capable of being fully automated and should selectively detect the parent drug while minimizing inaccuracies resulting from the cross-reactivity of its metabolites or from constituents in a sample suspected of containing the immunosuppressant drug.

SUMMARY

Some examples in accordance with the principles described herein are directed to methods for determining an immunosuppressant drug in a sample suspected of containing an immunosuppressant drug. The method comprises providing in combination in a medium the sample, a first monoclonal antibody for the immunosuppressant drug, and a second monoclonal antibody for the immunosuppressant drug. The second monoclonal antibody binds to a portion of the immunosuppressant drug other than the portion to which the first monoclonal antibody binds to the immunosuppressant drug. The medium is incubated under conditions for binding of the first monoclonal antibody and the second monoclonal antibody to the immunosuppressant drug. The medium is examined for the presence of an immunocomplex comprising the immunosuppressant drug, the first monoclonal antibody and the second monoclonal antibody. The presence and/or amount of the immunocomplex indicates the presence and/or amount of the immunosuppressant drug in the sample.

Some examples in accordance with the principles described herein are directed to methods for determining tacrolimus in a sample suspected of containing tacrolimus. The methods comprise providing in combination in a medium the sample, a first monoclonal antibody for tacrolimus, and a second monoclonal antibody for tacrolimus. The second monoclonal antibody binds to a portion of tacrolimus other than the portion to which the first monoclonal antibody binds to tacrolimus. The medium is incubated under conditions for binding of the first antibody and the second antibody to tacrolimus in the sample and the medium is examined for the presence of an immunocomplex comprising tacrolimus, the first monoclonal antibody and the second monoclonal antibody. The presence and/or amount of the immunocomplex indicates the presence and/or amount of tacrolimus in the sample.

Some examples in accordance with the principles described herein are directed to methods for determining tacrolimus in a sample suspected of containing tacrolimus. The methods comprise providing in combination in a medium the sample, a first monoclonal antibody for tacrolimus associated with magnetic particles, and a second monoclonal antibody for tacrolimus, which is associated with an enzyme. The second monoclonal antibody binds to a portion of tacrolimus other than the portion to which the first monoclonal antibody binds to tacrolimus. The medium is incubated under conditions for binding of the first antibody and the second antibody to tacrolimus in the sample and the medium is examined for the presence of an immunocomplex comprising tacrolimus, the first monoclonal antibody and the second monoclonal antibody. The presence and/or amount of the immunocomplex indicates the presence and/or amount of tacrolimus in the sample.

DETAILED DESCRIPTION OF SPECIFIC EMBODIMENTS

General Discussion

Figure 1:
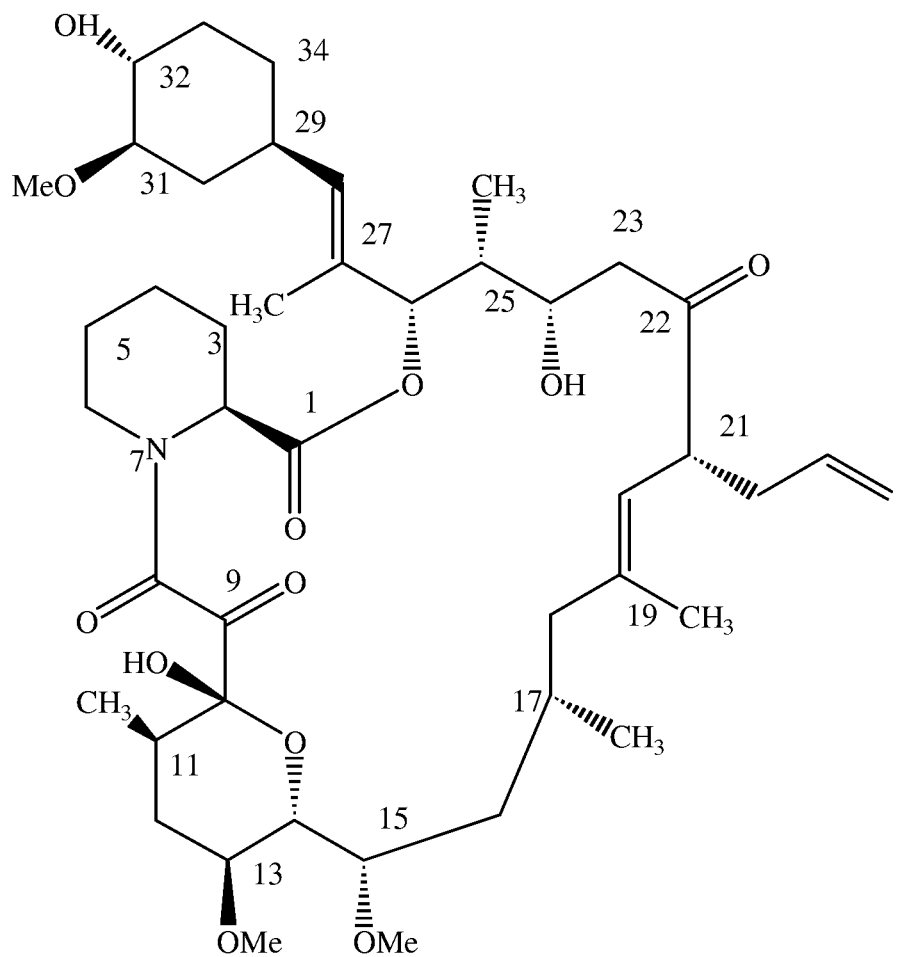
FIG. 1 is a chemical formula for tacrolimus with numbering.

The present inventor has discovered that monoclonal antibodies can be prepared that specifically bind to separate portions of immunosuppressant drug molecules. This discovery is surprising because immunosuppressant drugs are haptens, which are relatively small molecules (molecular weight less than about 2500, or less than about 2000, or less than about 1500, or less than about 1000) and are not considered to have more than one site to which an antibody can bind. In accordance with the principles described herein, at least two different antibodies can be prepared, which bind to separate portions of an immunosuppressant drug molecule at the same time. The phrase "antibody for the immunosuppressant drug" means an antibody that binds specifically to the immunosuppressant drug and does not bind to any significant degree to other substances that would distort the analysis for the immunosuppressant drug. Specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

Haptens are compounds capable of binding specifically to corresponding antibodies, but do not themselves act as immunogens (or antigens) for preparation of the antibodies. Consequently, a hapten is linked to an immunogenic carrier, which is employed to raise antibodies.

Preparation of monoclonal antibodies that bind to two different sites on an immunosuppressant drug at the same time enables the use of such antibodies in sandwich assays in which the immunosuppressant drug is simultaneously bound by the two different antibodies to form an immunocomplex. The ability to perform sandwich assays on immunosuppressant drugs enhances the sensitivity of an assay for the immunosuppressant drug. In addition, in the case of sandwich assays involving one monoclonal antibody bound to a support, the assay may be conducted in the presence of impurities and interfering substances of a sample because the support can be separated from the sample and washed after immunosuppressant drug has been allowed to bind to the monoclonal antibody of the support but before introduction of the second monoclonal antibody.

The term "immunosuppressant drugs" includes those that act on immunophilin such as, but not limited to, cyclosporin (including cyclosporin A, cyclosporin B, cyclosporin C, cyclosporin D, cyclosporin E, cyclosporin F, cyclosporin G, cyclosporin H, cyclosporin I), tacrolimus (FR-900506, FK506, PROGRAF®), sirolimus (rapamycin, RAPAMUNE®), and everolimus (RAD, CERTICAN®), for example.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Monoclonal antibodies can be prepared by techniques that are well known in the art such as preparing continuous hybrid cell lines and collecting the secreted protein (somatic cell hybridization techniques). Monoclonal antibodies may be produced according to the standard techniques of Köhler and Milstein, Nature 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites. This approach involves cloning and expressing nucleotide sequences or mutagenized versions thereof coding at least for the amino acid sequences required for specific binding of natural antibodies.

In one approach for the production of monoclonal antibodies, a first step includes immunization of an antibody-producing animal such as a mouse, a rat, a goat, a sheep, or a cow with the antigen, for example, with an immunogen. Immunization can be performed with or without an adjuvant such as complete Freund's adjuvant or other adjuvants such as monophosphoryl lipid A and synthetic trehalose dicorynomycolate adjuvant. A next step includes isolating spleen cells from the antibody-producing animal and fusing the antibody-producing spleen cells with an appropriate fusion partner, typically a myeloma cell, such as by the use of polyethylene glycol or other techniques. Typically, the myeloma cells used are those that grow normally in hypoxanthine-thymidine (HT) medium but cannot grow in hypoxanthine-aminopterin-thymidine (HAT) medium, used for selection of the fused cells. A next step includes selection of the fused cells, typically by selection in HAT medium. A next step includes screening the cloned hybrids for appropriate antibody production using immunoassays such as enzyme-linked immunosorbent assay (ELISA) or other immunoassays appropriate for screening.

The term "immunogenic carrier" means a group or moiety which, when conjugated to a hapten and injected into a mammal or otherwise employed as an immunogen, induces an immune response and elicits production of antibodies that bind to the hapten. Immunogenic carriers are also sometimes referred to as antigenic carriers. In some examples in accordance with the principles described herein, immunogens comprising immunogenic carriers, including poly(amino acid) and non-poly(amino acid) immunogenic carriers, linked to an immunosuppressant compound at a particular position are synthesized and used to prepare antibodies.

The molecular weight range (in Daltons) for poly(amino acids) that are immunogenic carriers is about 5,000 to about 10,000,000, or about 20,000 to about 600,000, or about 25,000 to about 250,000 molecular weight, for example. Poly(amino acid) immunogenic carriers include proteins such as, for example, albumins, serum proteins, e.g., globulins, ocular lens proteins and lipoproteins. Illustrative proteins include, but are not limited to, bovine serum albumin (BSA), keyhole limpet hemocyanin (KLH), egg ovalbumin, and bovine gamma-globulin (BGG), for example. Non-poly(amino acid) immunogenic carriers include polysaccharides, nucleic acids and particles (biologic and synthetic materials). A wide variety of immunogenic carriers are disclosed in Davalian, et al., U.S. Pat. No. 5,089,390, column 4, line 57 to column 5, line 5, which is incorporated herein by reference.

As mentioned above, the immunogenic carrier may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly (amino acid) residues and/or lipid residues.

As mentioned above, in some examples in accordance with the principles described herein, the immunogenic carrier may be linked to the immunosuppressant compound at a predetermined position on the immunosuppressant compound by means of a linking group. In some examples, the linking group may comprise about 2 to about 50 atoms, or 4 to about 30 atoms, not counting hydrogen and may comprise a chain of from 2 to about 30 atoms, or 3 to about 20 atoms, each independently selected from the group normally consisting of carbon, oxygen, sulfur, nitrogen, and phosphorous. Part or all of the linking group may be a portion of the molecule being linked to the immunosuppressant compound such as, but not limited to, an amino acid residue on a poly(amino acid), for example. In some examples, the linking group comprises an oxime functionality.

The number of heteroatoms in the linking group may be in the range from 0 to about 20, or 1 to about 15, or about 2 to about 10. The linking group may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. One specific embodiment of a linking group comprising heteroatoms is an oxime functionality as mentioned above.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. Various linking groups are well known in the art; see, for example, Cautrecasas, *J. Biol. Chem.* (1970) 245:3059.

Tacrolimus as a Specific Example

The following specific description is by way of illustration of, and not as a limitation on, the scope of the present invention. Selection of immunosuppressant drugs, and tacrolimus in particular, is also by way of illustration and not limitation as the present invention has general application to detection of any hapten that has spatially separated regions to which antibodies can be raised and to which such raised antibodies will bind specifically during an assay for the compound.

Figure 2:
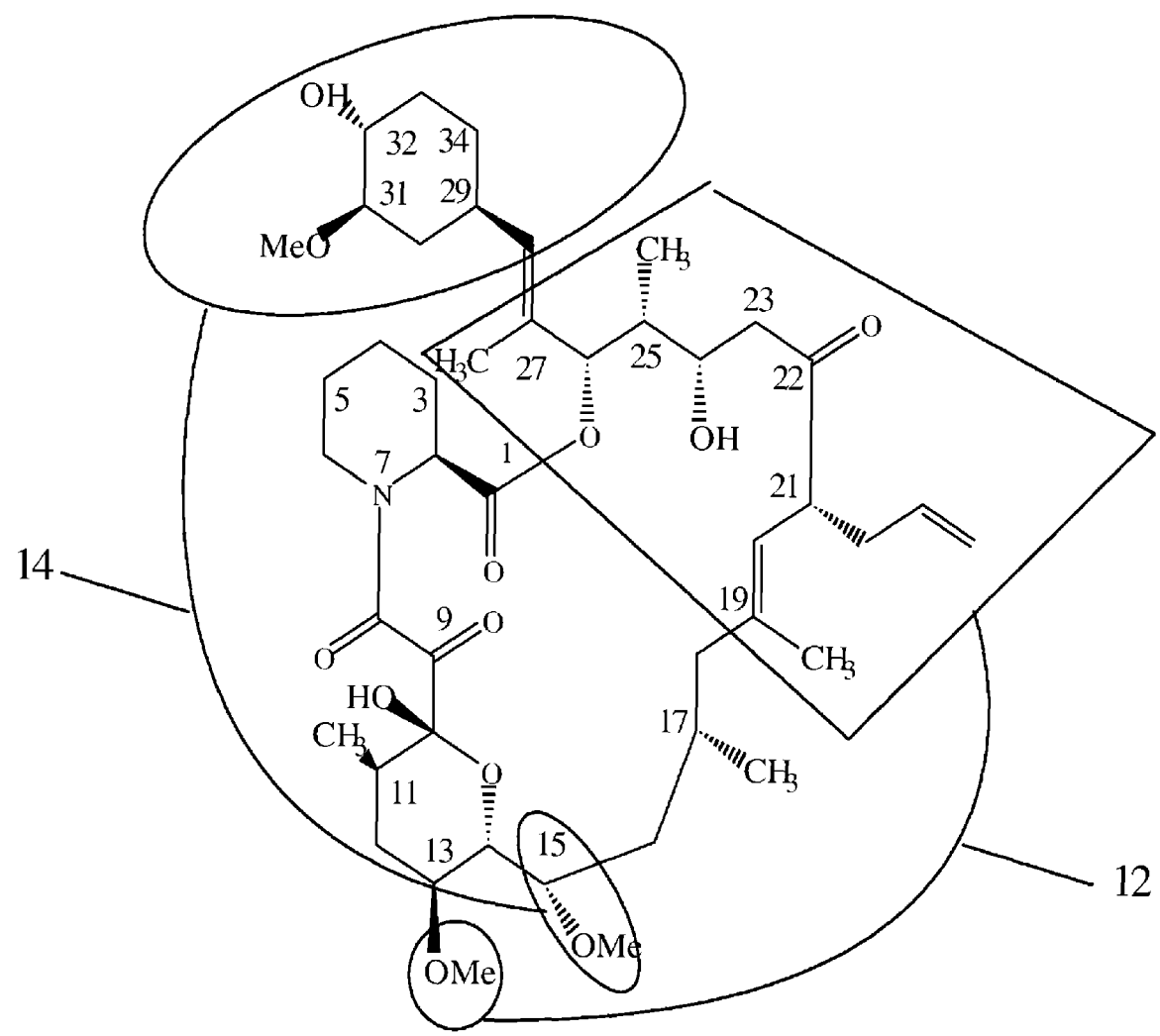
FIG. 2 is the chemical formula of FIG. 1 depicting portions of the molecule to which monoclonal antibodies bind in accordance with the principles described herein.

Monoclonal antibodies may be prepared that bind to separate portions of the tacrolimus molecule (FIG. 1). The separate portions to which the monoclonal antibodies bind may be determined, for example, by cross-reactivity studies using metabolites of tacrolimus. Referring to FIG. 2, one monoclonal antibody that may be prepared binds to a portion of tacrolimus (region 14) consisting essentially of the C29-C34 ring including the methoxy and hydroxy substituents and C15 including the methoxy substituent. Another monoclonal antibody may be prepared that binds to a portion of tacrolimus consisting essentially of the methoxy of the C10-C14 ring and C19-C27 of the C1-C26 ring including the C22 keto oxygen and also including the C24 hydroxy group and the C26 ester oxygen (region 12). Examination of the tacrolimus structure by three-dimensional analysis reveals the conformation of regions 12 and 14.

A monoclonal antibody directed to region 14 may be prepared from an immunogen in which tacrolimus at a position in the C19-C27 region of the tacrolimus molecule is linked, either directly by a bond or through the intermediacy of a linking group, to an immunogenic carrier.

In a specific example, by way of illustration and not limitation, in accordance with the principles described herein, tacrolimus at the C22 position of the tacrolimus molecule is linked, either directly by a bond or through the intermediacy of a linking group, to an immunogenic carrier. In a particular example, by way of illustration and not limitation, the keto group at the C22 position is reacted with an amine to produce an oxime. The amine may be, but is not limited to, carboxymethoxylamine, for example.

In one approach the reaction of tacrolimus with carboxymethoxylamine produces a carboxymethyl oxime. In this particular example, tacrolimus may be reacted with carboxymethoxylamine in an alcoholic medium such as, e.g., methanol, ethanol or propanol, in the presence of a buffer salt such as, e.g., sodium acetate, to give the carboxymethyl oxime. This oxime may be linked to an immunogenic carrier such as, e.g., a high molecular weight protein, which may be, but is not limited to, bovine serum albumin, thyroglobulin, ovalbumin, fibrinogen, or keyhole limpet hemocyanin, for example. In one example, the protein is keyhole limpet hemocyanin.

In an example, a method of preparation of the conjugate of tacrolimus with a high molecular weight protein is as follows: (1) preparation of the carboxymethyl oxime of tacrolimus as described above; (2) activating the carboxymethyl oxime to produce a reactive N-hydroxysuccinimide ester; and (3) reacting the N-hydroxysuccinimide ester with the high molecular weight protein to produce the conjugate. The activation of the carboxymethyl oxime to produce the N-hydroxysuccinimide ester is performed, for example, by using a coupling agent such as a water-soluble carbodiimide such as, for example, 3-(3-dimethylaminopropyl 1-ethyl-3-dimethylaminopropyl)-carbodiimide hydrochloride (EDAC).

In another example, a conjugate of tacrolimus derivatized at a carbon atom within the C19-C27 region of tacrolimus is a bromoacetyl derivative. The preparation of bromoacetyl derivatives of tacrolimus comprises (1) reacting tacrolimus with carboxymethoxylamine to produce a carboxymethyl oxime derivative of tacrolimus, (2) activating the carboxymethyl oxime to produce a reactive N-hydroxysuccinimide ester, and (3) reacting the N-hydroxysuccinimide ester with the trifluoroacetic acid salt of bromoacetyl ethylenediamine to produce a bromoacetyl derivative. The carboxymethyl oxime derivative used in this method is prepared as described above. Such bromoacetyl derivatives can be used to produce protein conjugates of tacrolimus by reacting the bromoacetyl moiety with a sulfhydryl group of a protein.

The monoclonal antibody for region 14 may be identified by a screening method as follows: The binding region of an antibody clone was identified based on its binding properties to different tacrolimus derivatives such as metabolites and immunogens. Region 14 was identified as the binding region for the 14H04 clone based on the following: (a) the immunogen employed had an immunogenic carrier protein linked through the C22 keto group of tacrolimus, (b) tacrolimus C22 oxime exhibits strong binding to monoclonal antibody 14H04 indicating that antibody binding does not occur near the C22 region (altering the region did not interrupt antibody binding), (c) tacrolimus C32 carbamate compound did not bind monoclonal antibody 14H04 and metabolites involving demethylation of C31 methoxy group drastically reduced the antibody binding, both of which indicate that 14H04 binds the C29-34 ring, and (d) no cross-reactivity with 15-O-demethyl tacrolimus indicates that 14H04 binds to the C15 neighboring region (altering the 15-O-methyl group removed the binding ability of the antibody).

A monoclonal antibody directed to region 12 may be prepared from an immunogen in which tacrolimus at a position in the C29-C34 region of the tacrolimus molecule is linked, either directly by a bond or through the intermediacy of a linking group, to an immunogenic carrier. The linking groups and the procedures for linking are as described above for linking through a position in the C19-C27 region of tacrolimus. In one example a moiety is linked to tacrolimus through position C32 of the tacrolimus molecule employing the hydroxy group.

The monoclonal antibody for region 12 may be identified by the following screening method. Region 12 was identified as the binding region for the 1E2 clone based on the following: (a) the immunogen employed was linked through C32 and altering C32 (e.g., tacrolimus C32 carbamate compounds) does not change the binding of monoclonal antibody 1E2, (c) 1E2 has 100% binding to C32 ester derivatives of tacrolimus, and (d) altering the C31 methoxy group (31-O-desmethyl) does not decrease binding of monoclonal antibody 1E2. All of the above indicate that monoclonal antibody 1E2 does not bind the C29-C34 ring o tacrolimus. Modification of the hydroxyl group linked to C24 weakened the binding of monoclonal antibody 1E2 to tacrolimus. Tacrolimus C22 oxime compound does not bind to 1E2, which indicates that monoclonal antibody 1E2 binds to the C22-C24 region of tacrolimus. Alteration of the C13 methoxy group as in the case of M1 (13-O-desmethyl) and MVI (13, 31 didesmethyl) removed the binding of monoclonal antibody 1E2 to tacrolimus, indicating that monoclonal antibody 1E2 binds to the C13 region of tacrolimus.

In view of the above, monoclonal antibodies 1E2 and 14H04 have separate binding domains on the tacrolimus molecule, which allow a sandwich assay for the tacrolimus drug.

Measurements of tacrolimus derivatives by the ACMIA assay format were carried out according to the following procedure. Metabolites were obtained from Isotechnika Pharma Inc (Alberta, Canada) and Dr. Christistians Laboratory at University of Colorado in Denver, Colo. The tacrolimus derivative compounds such as immunogens were obtained from Siemens AG (Glasgow, Del.). The metabolite and immunogen cross-reactivity was measured using the ACMIA methodology described in U.S. Pat. No. 7,186,518, the relevant disclosure of which is incorporated herein by reference. Briefly, both clones were conjugated to β-galactosidase using a standard heterobifunctional SMCC (succinimidyl trans-4-(N-maleimidylmethyl)cyclohexane-1-carboxylate) linker according to known techniques. Chrome particles (immunoassay solid phase) were prepared by conjugating tacrolimus analogs to bovine immunoglobulin and then to polyaldehyde dextran coated chromium dioxide particles. The tacrolimus analog used for monoclonal antibody 14H04 was a tacrolimus C22 oxime compound. The analog used for monoclonal antibody 1E2 was a tacrolimus C32 fluorescein derivative immobilized on anti-fluorescein antibody coated chromium dioxide particles. The cross reactivity was detected by testing the samples containing spiked metabolites and other tacrolimus derivatives such as the immunogens. The assay signals obtained from the samples containing the spiked metabolites were compared to the signals obtained from the samples containing tacrolimus standards. Cross-reactivity was determined by dividing the apparent tacrolimus concentration by the concentration of added metabolite and expressing the result as a percentage.

It should be noted that a sandwich assay in accordance with the principles described herein should exhibit a lower cross-reactivity with metabolites of tacrolimus as compared to a competitive assay utilizing one or the other of the above monoclonal antibody reagents. In a sandwich assay, a metabolite needs to bind to both antibodies to exhibit cross-reactivity. If a metabolite binds to only one antibody and not the other (or has weak binding to the other), no assay signal is generated and, hence, no cross-reactivity is demonstrated. If a metabolite exhibits 100% binding to one antibody but has a weaker binding (e.g., 30%) to the other, the cross-reactivity measured by the assay is the weaker binding (i.e., 30%). Furthermore, if a metabolite exhibits low binding (e.g., 40%) to one antibody and has an even lower binding (e.g., 20%) to the other antibody, the cross-reactivity in a sandwich assay should be lower than the lower binding (in the above example, 40%×20%=8%). In cross-reactivity studies, the two antibodies, 1E2 and 14H04, exhibit different cross-reactivity profiles with metabolites M1 13-O-desmethyl-tacrolimus, MII, 31-O-desmethyl Tacrolimus, MIII 15-O-desmethyl-tacrolimus, MIV 12-OH-tacrolimus, M-VI 13,31-O-didesmethyl-tacrolimus, and M-VII 15,31-O-didesmethyl-tacrolimus. The cross-reactivity measured in a sandwich assay should be equal to or lower than that of the antibody that exhibits lower binding to a metabolite.

General Description of Assays for an Immunosuppressant Drug

As mentioned above, examples in accordance with the principles described herein enable a sandwich assay for the determination of an immunosuppressant drug in a sample suspected of containing the immunosuppressant drug. In the sandwich assay, two monoclonal antibodies are employed, each of which bind at the same time to separate regions of the immunosuppressant drug molecule to form an immunocomplex. Detection of the immunocomplex permits the determination of the immunosuppressant drug in the sample.

The sample to be tested is usually a biological sample. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid. In some examples the sample is whole blood, plasma or serum.

Prior to the assay, or in some instances during the assay, the sample may be subjected to one or more pretreatments to lyse cells and/or to release immunosuppressant drug from endogeneous binding substances. Lysing cells may be accomplished by use of a hemolytic agent, which is a compound or mixture of compounds that disrupts the integrity of the membranes of red blood cells thereby releasing intracellular contents of the cells. Hemolytic agents include, but are not limited to, non-ionic detergents, anionic detergents, amphoteric detergents, low ionic strength aqueous solutions (hypotonic solutions), bacterial agents, and antibodies that cause complement dependent lysis, for example.

Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis (ethoxylate-block-propoxylate) tetrol, IGEPAL®, MERPOL®, poly(ethylene glycol), 2-[ethyl [(heptadecafluorooctyl)sulfonyl]amino]ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanoliamin, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

The nature and amount or concentration of hemolytic agent employed depends on one or more of the nature of the sample, the nature of the immunosuppressant drug, the nature of the rest of the reagent components, and the reaction conditions, for example. The amount of the hemolytic agent is at least sufficient to cause lysis of red blood cells to release contents of the cells. In some examples the amount of the hemolytic agent is about 0.0001% to about 0.5%, about 0.001% to about 0.4%, about 0.01% to about 0.3%, about 0.01% to about 0.2%, about 0.1% to about 0.3%, about 0.2% to about 0.5%, or about 0.1% to about 0.2%, for example (percent is weight/volume).

The releasing agent is a compound or mixture of compounds that displaces the immunosuppressant drug from endogenous binding moieties. The releasing agent can, and does in many instances, displace metabolites of the immunosuppressant drug from endogenous binding moieties. In many examples the releasing agent has high binding affinity to the endogenous binding proteins so that it readily displaces the immunosuppressant drug, and its metabolites where desired, from endogenous binding proteins. In addition, the releasing agent does not bind to any significant degree to a monoclonal antibody for the drug that is used in an assay. By the phrase "does not bind to any significant degree" is meant that the extent of binding should be low enough so that an accurate assay for the drug may be carried out. The releasing agent, therefore, may be any moiety, either a single compound or a mixture of compounds, which accomplishes the desired result of displacement with no significant binding to an assay antibody.

In some examples the releasing agent is an analog, including structural analogs, of the immunosuppressant drug. An immunosuppressant drug analog is a modified drug that can displace the analogous immunosuppressant drug from a binding protein but does not compete to any substantial degree for a monoclonal antibody for the immunosuppressant drug. The modification provides means to join an immunosuppressant drug analog to another molecule. In an example, the immunosuppressant drug analog may be, for example, the immunosuppressant drug conjugated to another molecule through a linking group. For immunosuppressant drugs that comprise a hydroxy or carboxylic acid functionality, the releasing agent may be an ester of the immunosuppressant drug, which has a high binding affinity for endogenous binding proteins relative to the immunosuppressant drug to be detected and which has no significant binding affinity for an antibody for the immunosuppressant drug. For example, in a determination for tacrolimus, an ester of tacrolimus may be employed as the releasing agent so long as it meets the above requirements. A structural analog is a moiety that has the same or similar structural or spatial characteristics as the immunosuppressant drug such that the structural analog accomplishes the same or similar result as the analog of the immunosuppressant drug. The structural analog may be, for example, another compound that is related to the immunosuppressant drug. For example, in a determination for tacrolimus, an ester of sirolimus may be employed as the releasing agent. The ester may be, for example, a carbamate, a carbonate, an ester of a $C_1$ to $C_6$ carboxylic acid, and the like. See, for example, U.S. Pat. No. 7,186,518, the relevant disclosure of which is incorporated herein by reference. Other examples of releasing agents include [$Thr_2$, $Leu_5$, D-$Hiv_8$, $Leu_{10}$]-cyclosporin A for cyclosporin A, FK506 for sirolimus, sirolimus for FK506, and the like. See, for example, U.S. Pat. No. 6,187,547, the relevant disclosure of which is incorporated herein by reference.

The concentration of the releasing agent in the medium is that sufficient to achieve the desired result of displacing the immunosuppressant drug, and in some instances the metabolites of the immunosuppressant drug, from endogenous binding moieties to render the drug and metabolites accessible for binding to an antibody for the drug as discussed above. The amount or concentration of the releasing agent employed depends on one or more of the nature of the sample, the nature of the immunosuppressant drug, the nature of the drug metabolites, the nature of other reagent components, and the reaction conditions, for example. In some embodiments the amount of the releasing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume).

The assay is an immunoassay, which may be performed either without separation (homogeneous) or with separation (heterogeneous) of any of the assay components or products.

The homogeneous or heterogeneous assays are carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, or in the range of about 5 to about 10, or in the range of about 6.5 to about 9.5. The pH will usually be a compromise between optimum binding of the monoclonal antibodies and the immunosuppressant drug, and the pH optimum for other reagents of the assay such as members of the signal producing system, for example.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; for example.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures range from about 5° to about 99° C., or about 15° C. to about 70° C., or about 20° C. to about 45° C. The time period for the incubation is about 0.2 seconds to about 6 hours, or about 2 seconds to about 1 hour, or about 1 to about 5 minutes. The time period depends on the temperature of the medium and the rate of binding of the various reagents, which is determined by the association rate constant, the concentration, the binding constant and dissociation rate constant. Temperatures during measurements range from about 10° C. to about 50° C., or from about 15° C. to about 40° C.

The concentration of immunosuppressant drug analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentrations of the various reagents in the assay medium will generally be determined by the concentration range of interest of the immunosuppressant drug analyte. However, the final concentration of each of the reagents is normally determined empirically to optimize the sensitivity of the assay over the range. That is, a variation in concentration of analyte that is of significance should provide an accurately measurable signal difference. Considerations such as the nature of a signal producing system and the nature of the immunosuppressant analyte normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

In the assays discussed above, one or more labels are employed wherein the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the immunosuppressant drug being detected or to an agent that reflects the amount of the immunosuppressant drug to be detected. The label is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, as the case may be.

Suitable labels include, by way of illustration and not limitation, enzymes such as β-galactosidase, alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chrome particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members or one or more of the monoclonal antibodies can be bound to a support. A monoclonal antibody may be bound to a solid support in any manner known in the art, provided only that the binding does not substantially interfere with the ability to bind with a region of the immunosuppressant drug. In some examples, the label or other sps member or the monoclonal antibody may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the moiety to be coupled. The linking group may be one as described above for the linking of immunogen to an immunosuppressant drug molecule. Other methods of binding to a support may also be employed. For instance, a solid support may have a coating of a binder for a small molecule such as, for example, avidin or an antibody, where a small molecule such as, e.g., biotin or a hapten, can be bound to the moiety to be coupled or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, DENDRIMERS, and the like. Depending on the type of assay, the support may or may not be suspendable in the medium in which it is employed. Examples, by way of illustration and not limitation, of suspendable supports are polymeric materials such as latex, lipid bilayers or liposomes, oil droplets, cells and hydrogels, and magnetic particles, for example. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly (ethylene terephthalate), nylon, poly(vinyl butyrate), for example; either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, streptococcus, *Staphylococcus aureus*, and *E. coli*, viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chrome particles or latex particles.

The polymer particles can be formed of addition or condensation polymers. The particles will be readily dispersible in an aqueous medium and can be adsorptive or functionalizable so as to permit conjugation to a monoclonal antibody for an immunosuppressant drug, either directly or indirectly through a linking group. The linking group may be one as described above for the linking of immunogens to an immunosuppressant drug molecule. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The label and/or other sps member may be bound to one or both of the two different monoclonal antibodies. Bonding of the label to the sbp member may be accomplished by chemical reactions that result in replacing a hydrogen atom of the label with a bond to the monoclonal antibody or may include a linking group between the label and the monoclonal antibody. The linking group may be one as described above for the linking of immunogens to an immunosuppressant drug molecule. Other sps members may also be bound covalently to the monoclonal antibodies. For example, two sps members such as a fluorescer and quencher can each be bound, respectively, to the monoclonal antibodies where the fluorescer is bound to one of the monoclonal antibodies and a quencher is bound to the other of the monoclonal antibodies. When the two different monoclonal antibodies bind to the immunosuppressasnt drug, the formation of a sandwich complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include, but are not limited to, saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems addition of a substrate and/or a cofactor may be necessary.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the sirolimus compound present in a sample. Temperatures during measurements may range from about 10° to about 70° C., or from about 20° to about 45° C., or from about 20° to about 25° C. In one approach standard curves are formed using known concentrations of the analytes to be screened. As discussed above, calibrators and other controls may also be used.

The phrase "measuring the amount of an immunosuppressant drug" refers to the quantitative, semi-quantitative and qualitative determination of the immunosuppressant drug. Methods that are quantitative, semi-quantitative and qualitative, as well as all other methods for determining the immunosuppressant drug, are considered to be methods of measuring the amount of the immunosuppressant drug. For example, a method, which merely detects the presence or absence of the immunosuppressant drug in a sample suspected of containing the immunosuppressant drug, is considered to be included within the scope of the present disclosure. The terms "detecting" and "determining," as well as other common synonyms for measuring, are contemplated within the scope of the present disclosure.

In one example in accordance with the principles described herein, one of the monoclonal antibodies specific for a region of an immunosuppressant drug is bound to a support and the other of the monoclonal antibodies that is specific for a region of the immunosuppressant drug that is spatially separated from the region of the immunosuppressant drug to which the other monoclonal antibodies binds is bound to an sps member such as, for example, a label. The sample suspected of containing the immunosuppressant drug is combined in a suitable medium with the two conjugated monoclonal antibodies and the medium is incubated. Then, the medium is examined for the one or both of the presence and amount of an immunocomplex formed by the two different monoclonal antibodies and the immunosuppressant drug from the sample. The support may or may not be separated from the medium prior to the examination. The presence and/or amount of the immunocomplex is determined by determining the presence and/or amount of the label in the medium or on the support.

In one particular example, a capture assay is employed. In this assay format, one monoclonal antibody is covalently bound to a magnetic particle such as, for example, a chrome (chromium dioxide) particle. The sample is incubated with these particles to allow the immunosuppressant drug in the sample to bind to the monoclonal antibody on the magnetic particle. Subsequently, a second monoclonal antibody conjugated to an enzyme such as, for example, β-galactosidase, is incubated with the magnetic particles. After application of a magnet and washing of the magnetic particles, the amount of enzyme that is bound to the magnetic particles is measured and is directly related to the presence and/or amount of the immunosuppressant drug in the sample. In this approach substrate of the reporter enzyme is added to the final reaction container, and the enzyme activity is measured spectrophotometrically as a change in absorbance over time.

In an alternative approach, the magnetic particle reagent is added in an excess amount, i.e., an amount greater than that required to bind all of the immunosuppressant drug that might be present in the sample. Then, a magnet is applied to separate the magnetic particles from the medium and the magnetic particles are washed and resuspended in assay medium. The enzyme conjugated to the second monoclonal antibody is added and the medium is incubated followed by signal determination as described above.

In another example, by way of illustration and not limitation, chemiluminescent particles are employed, which comprise the chemiluminescent compound associated therewith such as by incorporation therein or attachment thereto. One of the monoclonal antibodies for the immunosuppressant drug is bound to the particles such as through the intermediacy of a polysaccharide coating the particles. The other monoclonal antibody that binds to the immunosuppressant drug is part of a biotin conjugate. Streptavidin is conjugated to a second set of particles having a photosensitizer associated therewith. The chemiluminescent particles are mixed with a sample suspected of containing the immunosuppressant drug and the photosensitizer particles. The reaction medium is incubated to allow the particles to bind to the immunosuppressant drug by virtue of the binding of the monoclonal antibodies to the immunosuppressant drug. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the immunosuppressant drug, it is activated by singlet oxygen and emits luminescence. The medium is then examined for the presence and/or the amount of luminescence or light emitted, the presence thereof being related to the presence and/or amount of the immunosuppressant drug in a sample.

Kits for Conducting Assays

The reagents for conducting a particular assay may be present in a kit useful for conveniently performing an assay for the determination of an immunosuppressant drug analyte. In one example, a kit comprises in packaged combination reagents for analyzing for the analyte, the nature of which depend upon the particular assay format. The reagents may include, for example, one or more monoclonal antibodies in accordance with the principles described herein, which may be conjugated to a label or a support. The reagents may each be in separate containers or various reagents can be combined in one or more containers depending on the cross-reactivity and stability of the reagents. The kit can further include other separately packaged reagents for conducting an assay such as additional binding members and ancillary reagents.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method in accordance with the present embodiments as described above.

The phrase "at least" as used herein means that the number of specified items may be equal to or greater than the number recited. The phrase "about" as used herein means that the number recited may differ by plus or minus 10%; for example, "about 5" means a range of 4.5 to 5.5. The designation "first" and "second" is completely arbitrary and is not meant to suggest any order or ranking among any members of a group to which the above language pertains such as, for example, "first and second monoclonal antibodies" or "first monoclonal antibody" and "second monoclonal antibody."

The following examples further describe the specific embodiments of the invention by way of illustration and not limitation and are intended to describe and not to limit the scope of the invention. Parts and percentages disclosed herein are by volume unless otherwise indicated.

EXAMPLES

All chemicals were purchased from the Sigma-Aldrich Company (St. Louis Mo.) unless otherwise noted. Tacrolimus was obtained from Astellas Pharma US, Inc., Deerfield, Ill.

Testing was carried out using the DIMENSION® RxL analyzer, available from Siemens AG, Newark Del. The instrument was employed using enzymatic detection system with sandwich immunoassay format. In the embodiment of the sandwich method used herein and discussed in more detail below, binding between a labeled antibody (Ab) conjugated to an enzyme (conjugate) and tacrolimus drug (TACRO) in patient samples and subsequent binding of the resulting immunocomplex with a capture antibody on chrome particles determined the amount of tacrolimus in the patient samples. The unbound tag antibody enzyme conjugate was removed automatically by 3-4 mix/wash and magnetic separation cycles. The enzymatic activity from conjugate remaining on the chrome particles was measured and was directly proportional to the amount of tacrolimus in the patient sample.

Example 1

Determination of Tacrolimus Using Automated ACMIA Sandwich Assay

Preparation of Tacrolimus-Keyhole Limpet Hemocyanin Conjugates. To a solution of tacrolimus monooxime (32.3 mg, 36.8 µmol) in 1.05 mL of anhydrous dimethylformamide was added 1-ethyl-3-(3-dimethylaminopropyl)carbodiimide hydrochloride (EDAC) (11 mg, 57.4 µM, 1.5 equiv.) and N-hydroxysuccinimide (7.3 mg, 63.4 µM, 1.7 equiv.). Linkage was at the C22 position of the tacrolimus molecule. The reaction was stirred at room temperature for 1 hour under argon. The mixture was then added dropwise via a syringe to a solution of keyhole limpet hemocyanin (74 mg, 54% pure) in 5.0 mL of phosphate buffered saline (0.1 M, pH 8.0) and 0.25 mL of dimethylformamide. After stirring at room temperature for 2 hours, the resulting suspension was dialyzed (1×4 L, 4° C., 2 hours) against PBS (phosphate buffered saline) (10 mM, pH 7.0).

The resulting mixture was then extracted 3 times with methylene chloride to remove any trace amount of unreacted tacrolimus monooximes. Quantitative analysis of the mixture was conducted using bicinchoninic acid (BCA) protein assay solution to give 50 mg of immunogen in 8 ml of PBS (10 mM, pH 7.0).

Determination of the hapten number using the TNBS method (A.F.S.A. Habeeb, Anal. Biochem. 14:328 (1966)) gave a hapten number of 1300. The immunogen was immediately frozen using a dry ice-acetone bath and kept at −20° C. for storage.

An immunogen mixture containing three positional isomers of tacrolimus (KLH linked at position C32, KLH linked at position C24 and KLH linked at positions C32 and C24) was prepared as follows: Tacrolimus (301.3 mg) in a round bottomed flask was dried in vacuum for 1.5 hours. To the flask was added a stirrer bar, succinic anhydride (568.2 mg), 4-(dimethylamino)pyridine (46.3 mg), dichloromethane (2 mL, anhydrous) and pyridine (2.093 mL). The reaction mixture was stirred at room temperature (24° C.) under nitrogen atmosphere for 24.5 hours. Three positional isomers were the products of this reaction: tacrolimus-32-succinate, tacrolimus-24-succinate and tacrolimus-24, 32-di-succinate. Once reaction was stopped, solvent was removed by rotary evaporation and the product was dried further by vacuum pump for two hours.

To a vial was added the tacrolimus-succinate mixture from above (2.5 mg, 2.8 µmoles), N-hydroxysuccinimide (1.0 mg, 8.7 µmoles) and anhydrous acetonitrile (250 µL). The mixture was capped and stirred at room temperature. To the stirring mixture was added N,N-dicyclohexylcarbodiimide (3.0 mg, 15 µmoles). The vial was capped and the mixture was stirred at room temperature.

After 2 hours, the mixture was evaporated to dryness. The resulting material was dissolved in anhydrous N,N-dimethylformamide (250 µL). This was the working solution of activated FK506-succinate.

In a 20 mL vial was added a solution of KLH (8 mg) in 8 mL of 10 mM phosphate buffer pH 8, and DMF (1.5 mL). The mixture was chilled to about 4° C. and 200 of the working solution from above was added dropwise with stiffing to the chilled solution. The mixture was stirred for 16-24 hours at 4° C. and then was diluted to 30 mL with water, desalted with two CENTRICON® 30 filters, and reconstituted with fresh water 3 more times. The final material was diluted to 10 mL with water. Protein concentration was determined by BCA protein assay method.

Preparation of Monoclonal Antibody to Tacrolimus. Monoclonal antibodies that bind to separate portions of the tacrolimus molecule were prepared as follows. The immunogen was tacrolimus-keyhole limpet hemocyanin conjugate prepared as described above. This immunogen was used to immunize Balb/c mice. The first immunization was 25 µg in a volume of 200 µl with monophosphoryl lipid A and synthetic trehalose dicorynomycolate adjuvant (RIBI MPL+ TDM Emulsion, RIBI ImmunoChem Research Inc., Hamilton Mont.) intraperitoneally. Five weeks later a boost immunization was given with 25 µg of the immunogen in 200 µl of monophosphoryl lipid A and synthetic trehalose dicorynomycolate adjuvant intraperitoneally. Subsequently, after another 8 weeks, a prefusion boost was given of the 25 µg of the immunogen in 200 µl of Hanks' Balanced Salt Solution intravenously and intraperitoneally.

Three days later, fusion was performed by standard methods using a nonsecreting murine myeloma designated P3x63-AG8.653. Cloning was carried out by standard methods.

The clones were screened by the following reverse ELISA immunoassay procedure according to the following protocol. Plates were coated with polyclonal goat anti-mouse IgG (IgG+IgA+IgM) (Zymed Laboratories, South San Francisco Calif.) at 5 µg/ml in phosphate buffered saline at 100 µl per well. Plate coating was performed for 2 hours or more at room temperature or overnight at about 4° C.; the plates could be stored wrapped in film at about 4° C. for several days. The plates were then flicked dry and blocked with 300 µl per well of blocking buffer diluent (0.5% bovine serum albumin, 0.05% TWEEN® 20 in PBS). Plate blocking was performed by incubation for 15 minutes or more at room temperature with plate shaking. The plates were then flicked dry. The monoclonal antibody to be screened was then added to each well as follows: 50 µl per well of blocking buffer diluent was added along with 50 µl per well culture supernatant transferred from the corresponding well in the fusion growth plate.

Incubation was for about 1 hour at room temperature with shaking. The plate was washed using a TITERTECK PLUS® plate washer with S20 stacker with the washing buffer being PBS with 0.05% TWEEN® 20. An enzyme conjugate of tacrolimus covalently coupled to glucose-6-phosphate dehydrogenase diluted in blocking buffer diluent to 1:4000 was added at 100 µl per well. Incubation was performed for about 1 hour at room temperature with shaking. The plate was then washed and a chromogenic solution was added at a volume of 100 µl per well. The chromogenic solution contained 0.593 mM p-iodonitrotetrazolium violet, 0.02 M NAD, 0.033 M glucose-6-phosphate, 0.055 M Tris, 0.02% sodium azide, and a 1:4000 dilution of diaphorase (lipoyl dehydrogenase). BSA was present at 1% (vol/vol) of a 5% w/vol BSA solution. BSA was used to help prevent rapid precipitation of reduced p-iodonitrotetrazolium violet.

From the screening a hybridoma producing a suitable monoclonal antibody was selected. This is designated as 14H04 antibody.

Monoclonal antibody for tacrolimus designated 1E2 was prepared in a similar manner using an immunogen mixture having KLH linked at the C32, C24 and C32, and C24 positions of the tacrolimus molecule as described above.

Preparation of hemolytic pretreatment solution. This pretreatment solution contained 5 µg/mL of sirolimus (SIRO), 6.8 mg/mL PIPES™ 1.5 sodium salt, 0.3 mg/mL EDTA Disodium, 1.0 mg/mL Saponin, 0.2% PROCLIN® 300, 0.024 mg/mL Neomycin sulfate and 0.99 mg/mL $NaN_3$, pH 6.5. The SIRO concentration in the final reaction mixture was 1.1 µg/mL. Table 1 shows the composition of the hemolysis reagent for use in hemolyzing a portion of a whole blood sample for assay for Tacrolimus (AI=as indicated). Chol is cholesterol and Trig is triglyceride.

TABLE 1

| Name | Qty. (per mL) | Function |
|---|---|---|
| Sirolimus | 5 µg | dissociates FK506 from binding protein |
| Sodium azide | 0.99 mg | matrix effect mitigation |
| PIPES ™ 1.5 sodium salt | 6.8 mg | buffer |
| EDTA disodium dihydrate | 0.3 mg | preventing clot-formation |
| Saponin | 1 mg | blood cell lysis |
| PLURONIC ® 25R2 | 0.9 mg | chol/Trig interference |
| PROCLIN ® 300 | 0.4 mg | preservative |
| Neomycin sulfate | 0.024 mg | preservative |

Preparation of anti-tacrolimus F(Ab')$_2$-β-galactosidase conjugate using 14H04 clone. Monoclonal anti-tacrolimus antibody 14H04 (prepared as described above) was fragmented to F(ab')$_2$ using lysyl-endopeptidase (Wako, Richmond, Va.) digestion and then conjugated to β-galactosidase using a standard heterobifunctional SMCC (succinimidyl trans-4-(N-maleimidylmethyl)cyclohexane-1-carboxylate) linker according to known techniques. The antibody conjugate solution contained approximately 2.0 µg/mL anti-tacrolimus antibody-β-galactosidase conjugate, 30 mg/mL protease free bovine serum albumin, 0.126 mg/mL $MgCl_2$, 0.03 mL/mL of ethylene glycol, 24.5 mg/mL HEPES, 38.5 mg/mL Na HEPES, 50 mg/mL NaCl and beta-gal mutein (inactivated beta-galactosidase), pH 7.8.

Magnetic chrome particle preparation. Chrome particles (immunoassay solid phase) were prepared by conjugating monoclonal anti-tacrolimus antibody 1E2 (prepared as described above) to glutaraldehyde coated chromium dioxide particles. The chrome reagent contains chrome particles and 60.4 mg/mL trehalose dihydrate and 7.2 mg/mL polyethylene glycol (PEG) 8000. Three chrome particle concentrations, namely 5, 2.5, and 1.67 mg/mL, were used in the study.

Sandwich tacrolimus assay. The principle and operation of the Sandwich assay for tacrolimus is as follows: A whole blood sample (50 µL) containing tacrolimus was combined with a hemolytic pretreatment reagent prepared as described above in a reaction vessel on the DIMENSION® RxL analyzer. The whole blood was sampled from a standard cup by first mixing the blood with the ultrasonic sample probe. The mixing of whole blood sample with the pretreatment solution ensured the hemolysis of the whole blood and the displacement of the protein-bound tacrolimus molecules from their binding sites.

Figure 3:
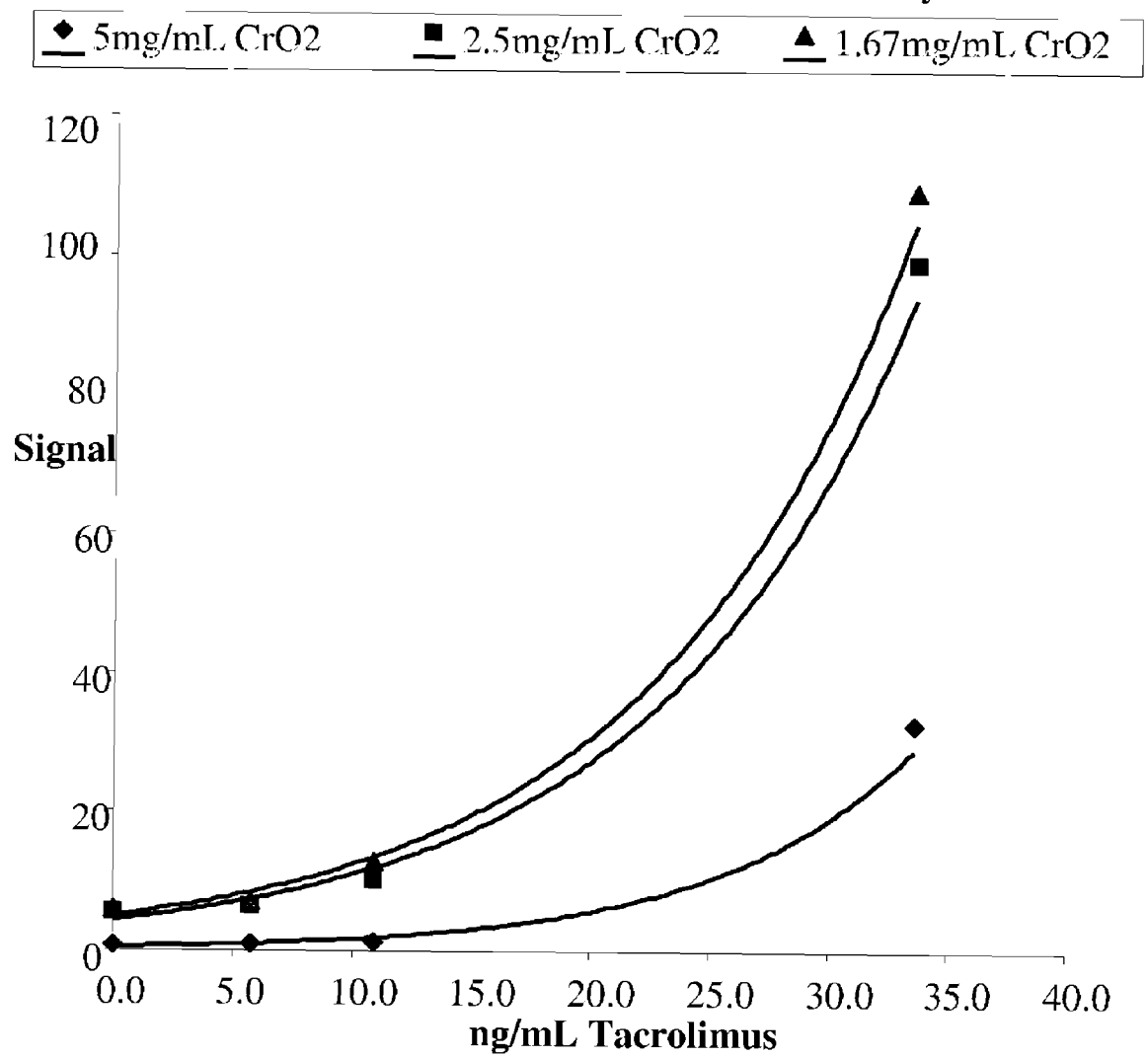
FIG. 3 is a graph depicting signal dose response curves of a tacrolimus sandwich immunoassay in accordance with the principles described herein.

Anti-tacrolimus F(ab')$_2$-β-galactosidase conjugate prepared using the 14H04 antibody clone (50 µL) was added the reaction vessels and the mixture was held for a period of time (35 seconds) and at a temperature of 43° C. to allow tacrolimus, if present, to react with the antibody enzyme conjugate. Chrome particles with immobilized 1E2 monoclonal antibody were added (50 µL) to the reaction vessels and were allowed to bind the tacrolimus-14H04F(ab')$_2$-β-galactosidase complex to form chrome-1E2 Ab::tarcrolimus::14H04 Ab sandwich. This reaction mixture was incubated for 14 minutes at a temperature of 43° C. before the automated magnetic separation, mix and wash cycles begin on the Dimension instrument. A total of 4 separation/wash cycles were employed to remove the unbound anti-tacrolimus F(ab')$_2$-β-galactosidase conjugate and debris from sample. The automated chrome washes were conducted on board using Chemistry Wash solution at pH 8.0 in HEPES buffer, both of which were provided for the DIMENSION® Heterogeneous Immunoassay Module. The washed chrome particles were then re-suspended in the Chemistry Wash solution by ultrasound mixing and a portion (54 µL) of the suspended chrome particles were transferred to a photometric cuvette to mix with a β-galactosidase substrate solution (chlorophenol red-β-D-galactopyranoside, or CPRG). The tacrolimus bound to the 14H04 anti-tacrolimus F(ab')$_2$-β-galactosidase conjugate on the chrome particle surface was detected by measuring the enzymatic rate of the conjugate in the presence of CPRG. The rate for each reaction vessel was measured bichromatically at 577 and 700 nm. Signal dose response curves of the tacrolimus sandwich immunoassay are depicted in FIG. 3.

Example 2

Determination of Tacrolimus Using Automated ELISA Sandwich Assay

Preparation of anti-tacrolimus Antibody-β-galactosidase conjugate using 1E2 clone. A mouse monoclonal anti-tacrolimus antibody, clone 1E2 (prepared as described above) was derivatized with the heterobifunctional linker SMCC (succinimidyl 4-(N-maleimidomethyl)cyclohexane-1-carboxylate (EMD Biosciences, Inc., La Jolla Calif.) in a milieu comprised of 10 mM sodium phosphate, pH 6.7 with added 300 mM sodium chloride. After allowing the derivatization reaction to progress for 60 minutes at 25° C., the resulting maleimide-activated antibody was re-purified by buffer-exchange into the above milieu to remove unreacted linker and free N-hydroxysuccinimide, followed by a concentration adjustment to 1.0 mg/mL.

Recombinantly-produced β-Galactosidase enzyme from *E. coli* (Roche Diagnostics, Indianapolis Ind.) was then dissolved at a concentration of 1.0 mg/mL, in the same phosphate/sodium chloride milieu, into which was mixed the maleimide-activated antibody at a 1:1 antibody:enzyme molar ratio. The mixture was stirred gently at 25° C. while the generation of conjugate species over time was monitored by chromatography using a 9.4×250 mm ZORBAX® GF-450 HPLC column (Agilent Technologies, Santa Clara Calif.). The conjugation reaction was quenched when small amounts of low molecular weight conjugate were generated. This quench was accomplished by the addition to the reaction mixture of sufficient quantities of N-ethylmaleimide (Thermo Fisher Scientific, Rockford Ill.) and hydrazine. The quenched reaction mixture was filtered through a 0.2 micron filter, concentrated to approximately 15 mg total protein/mL. The mixture was then purified by semi-preparative size exclusion chromatography using a 21.2×300 mm BIOSEP™-SEC-S-4000 HPLC column (Phenomenex, Torrance Calif.) using the same phosphate/sodium chloride conjugation reaction milieu as the mobile phase. Fractions containing the desired molecular weight conjugate material were pooled. The product conjugate pool was then diluted for use.

Figure 4:
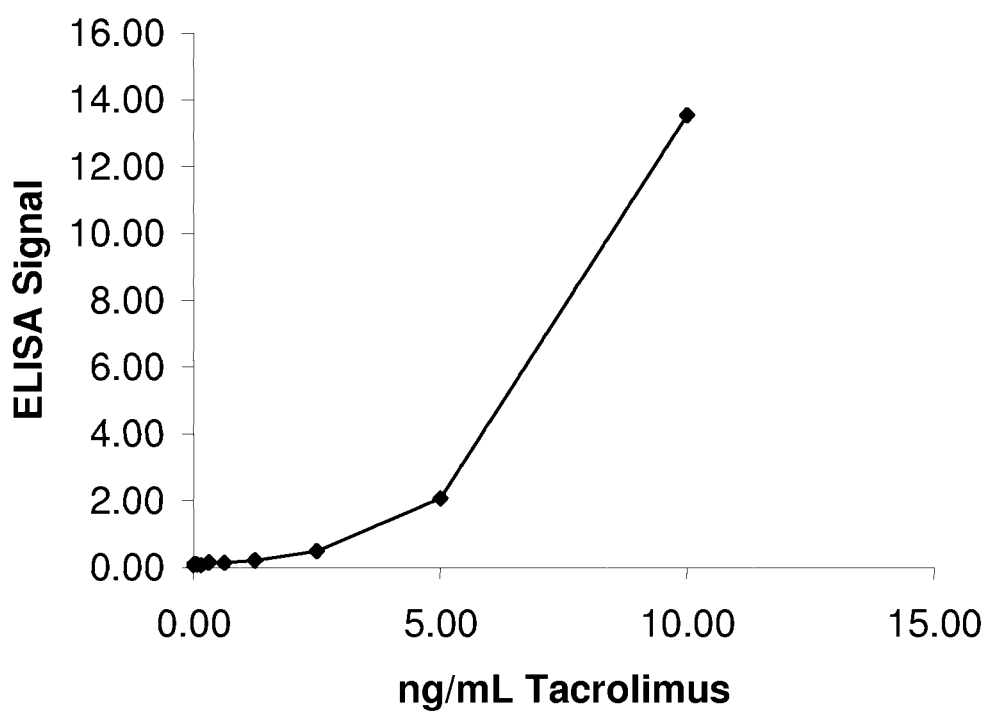
FIG. 4 is a graph depicting signal dose response curves of a tacrolimus ELISA sandwich immunoassay in accordance with the principles described herein.

Sandwich enzyme-linked immunosorbent assay (ELISA) for tacrolimus. The following steps are employed: Step 1: 50 μL of purified 14H04 (prepared as described above) (10 μg/mL in PBS) was coated on ELISA plates overnight at 4° C. Plates were washed using MilliQ water containing 0.05% TWEEN® 20. Step 2: 200 μL of PCT Blocker solution (0.5% Casein (milk protein) in phosphate buffer containing 0.05% TWEEN® 20) was added to each well and the media were incubated at room temp for 30 minutes. Plates were washed using MilliQ water containing 0.05% TWEEN® 20. Step 3: 50 μL of desired concentration of drug (FK506) diluted in PBS was added to the respective wells and the media were incubated at room temperature for 30 minutes. Plates were washed using MilliQ water containing 0.05% TWEEN® 20. Tacrolimus (TACR) drug concentrations tested were 0, 0.01, 0.02, 0.04, 0.08, 0.16, 0.31, 0.63, 1.25, 2.50, 5.0 and 10.0 ng/mL, respectively. Step 4: The monoclonal antibody 1E2-β-galactosidase conjugate (prepared in a manner similar to that described above) (1:300 diluted in PCT Blocker solution) was added and the media were incubated at room temp for 30 minutes. Plates were washed using MilliQ water containing 0.05% TWEEN® 20. Step 5: β-galactosidase substrate solution (chlorophenol red-β-D-galactopyranoside, or CPRG) was added to each well (100 μL/well). Step 6: The wells were read in plate reader at 577 nm every minute for 20 minutes. The results are summarized in FIG. 4 where the ELISA signal is in milliabsorbance units (mAU).

Control studies to rule out non-specific binding. Control studies to rule out non-specific binding were carried out under the experimental conditions as described above. In one study, monoclonal antibody 14H04 was coated on an ELISA plate, which was then washed. Tacrolimus and anti-tacrolimus 14H04F(ab')2-β-galactosidase conjugate were added and the resulting mixtures were incubated and washed as above. In a second study, monoclonal antibody 1E2 was coated on an ELISA plate, which was then washed. Tacrolimus and anti-tacrolimus 1E2-β-galactosidase conjugate were added and the resulting mixtures were incubated and washed as above. In a third study, no capture monoclonal antibody was coated on the ELISA plate, but tacrolimus drug and either of the above monoclonal antibody conjugates was added, with subsequent washing and incubation as described above. For all these control study, no ELISA signal was detected with the reads in the plate reader at 577 nm in the 20 minute reading period after the β-galactosidase substrate solution was added. These results indicate that no sandwich was formed under the conditions set forth.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for determining an immunosuppressant drug in a sample suspected of containing the immunosuppressant drug, the method comprising:
   (a) providing in combination in a medium:
      (i) the sample,
      (ii) a first monoclonal antibody for the immunosuppressant drug, and
      (iii) a second monoclonal antibody for the immunosuppressant drug, wherein the second monoclonal antibody binds to a portion of the immunosuppressant drug other than the portion to which the first monoclonal antibody binds to the immunosuppressant drug,
   (b) incubating the medium under conditions for binding of the first monoclonal antibody and the second monoclonal antibody to the immunosuppressant drug, and
   (c) examining the medium for the presence of an immunocomplex comprising the immunosuppressant drug, the first monoclonal antibody and the second monoclonal antibody, the presence and/or amount of the immunocomplex indicating the presence and/or amount of the immunosuppressant drug in the sample, wherein the immunosuppressant drug is selected from the group consisting of tacrolimus, cyclosporin, rapamycin and everolimus.

2. The method according to claim 1, wherein one of the first monoclonal antibody and the second monoclonal antibody comprises a member of a signal producing system.

3. The method according to claim 1, wherein one of the first monoclonal antibody and the second monoclonal antibody is bound to a support.

4. The method according to claim 1, wherein the immunosuppressant drug is tacrolimus and the first monoclonal antibody binds to a portion of tacrolimus consisting essentially of the C29-C34 ring including the methoxy and hydroxy substituents and C15 including the methoxy substituent.

5. The method according to claim 1, wherein the immunosuppressant drug is tacrolimus and the second monoclonal antibody binds to a portion of tacrolimus consisting essentially of the methoxy of the C10-C14 ring and C19-C27 of the C1-C26 ring including the C22 keto oxygen.

6. The method according to claim 1, wherein the immunosuppressant drug is tacrolimus and the first monoclonal antibody is raised against an immunogen comprising an immunogenic carrier linked to tacrolimus at C22.

7. The method according to claim 1, wherein the immunosuppressant drug is tacrolimus and the second monoclonal antibody is raised against an immunogen comprising an immunogenic carrier linked to tacrolimus at C32.

8. A method for determining tacrolimus in a sample suspected of containing tacrolimus, the method comprising:
(a) providing in combination in a medium:
(i) the sample,
(ii) a first monoclonal antibody for tacrolimus, and
(iii) a second monoclonal antibody for tacrolimus, wherein the second monoclonal antibody binds to a portion of tacrolimus other than the portion to which the first monoclonal antibody binds to tacrolimus,
(b) incubating the medium under conditions for binding of the first antibody and the second antibody to tacrolimus in the sample, and
(c) examining the medium for the presence of an immunocomplex comprising tacrolimus, the first monoclonal antibody and the second monoclonal antibody, the presence and/or amount of the immunocomplex indicating the presence and/or amount of tacrolimus in the sample.

9. The method according to claim 8, wherein one of the first monoclonal antibody and the second monoclonal antibody comprises a member of a signal producing system.

10. The method according to claim 8, wherein one of the first monoclonal antibody and the second monoclonal antibody is bound to a support.

11. A method for determining tacrolimus in a sample suspected of containing tacrolimus, the method comprising:
(a) providing in combination in a medium:
(i) the sample,
(ii) a first monoclonal antibody for tacrolimus associated with magnetic particles, and
(iii) a second monoclonal antibody for tacrolimus, wherein the second monoclonal antibody binds to a portion of tacrolimus other than the portion to which the first monoclonal antibody binds to tacrolimus and wherein the second monoclonal antibody is associated with an enzyme,
(b) incubating the medium under conditions for binding of the first monoclonal antibody and the second monoclonal antibody to tacrolimus, and
(d) examining the medium for the presence of an immunocomplex comprising tacrolimus and the first monoclonal antibody and the second monoclonal antibody, the presence and/or amount of the immunocomplex indicating the presence and/or amount of tacrolimus in the sample.

12. The method according to claim 11, wherein the first monoclonal antibody binds to a portion of tacrolimus consisting essentially of the C29-C34 ring including the methoxy and hydroxy substituents and C15 including the methoxy substituent and wherein the second monoclonal antibody binds to a portion of tacrolimus consisting essentially of the methoxy of the C10-C14 ring and C19-C27 of the C1-C26 ring including the C25 hydroxy and the C22 keto oxygen.

* * * * *